United States Patent [19]

Torck et al.

[11] 4,310,710

[45] Jan. 12, 1982

[54] PROCESS FOR MANUFACTURING AND RECOVERING METHYL TERT.BUTYL ETHER

[75] Inventors: Bernard Torck, Boulogne sur Seine; Alain Convers, Rueil-Malmaison; Lionel Asselineau, Paris; Michel Hellin, Andresy, all of France

[73] Assignee: Institut Francais du Petrole, Rueil-Malmaison, France

[21] Appl. No.: 121,565

[22] Filed: Feb. 14, 1980

[30] Foreign Application Priority Data

Feb. 14, 1979 [FR] France ............................ 79 103937

[51] Int. Cl.$^3$ ............................................ C07C 41/06
[52] U.S. Cl. .................................................... 568/697
[58] Field of Search .......................................... 568/697

[56] References Cited

U.S. PATENT DOCUMENTS 2,050,442  9/1937  Metzger ............................ 568/899
2,480,940  9/1949  Leum et al. ........................ 568/697
3,135,807  6/1964  Grasselli et al. .................... 568/697

OTHER PUBLICATIONS

Stinson, "Chem. and Eng. News", Jun. 25, 1979, pp. 35 and 36.

Primary Examiner—Joseph E. Evans
Attorney, Agent, or Firm—Millen & White

[57] ABSTRACT

Methyl tert.butyl ether is obtained by reacting an isobutene-containing C$_4$ cut with methanol and distilling the reaction product at a superatmospheric pressure of 7–30 atm. abs. to recover a top fraction and a bottom fraction containing methyl tert.butyl ether. The isobutene conversion rate and the purity of the ether are increased by recycling a portion of the top fraction to the reaction zone.

9 Claims, 1 Drawing Figure

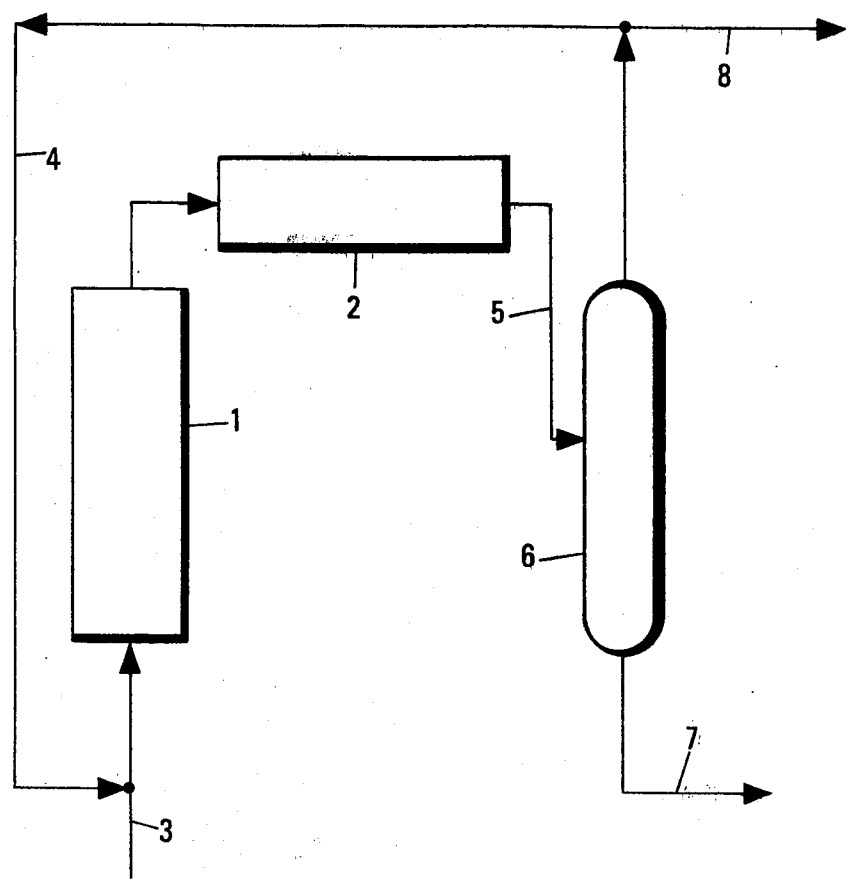

PROCESS FOR MANUFACTURING AND RECOVERING METHYL TERT.BUTYL ETHER

BACKGROUND OF THE INVENTION

This invention concerns the production and recovery of methyl tert. butyl ether, a valuable compound which can be used, for example, as high octane rating gasoline component.

It is well known to react isobutene with methanol in the presence of acid catalysts to obtain methyl tert. butyl ether (MtBE), as disclosed, for example, in the U.S. Pat. Nos. 2,480,940 and 3,037,052.

Isobutene is commonly used as a $C_4$ cut which comprises, in addition to isobutene, other mono-olefins and saturated hydrocarbons, and possibly small amounts of acetylenic or diolefinic hydrocarbons. This cut may be obtained, for example, by steam-cracking, catalytic cracking or dehydrogenation of hydrocarbons. Its isobutene content ranges, for example, from 5 to 70% by weight or more.

The reaction product of this balanced reaction normally contains, in addition to MtBE, unconverted methanol and isobutene, as well as the other hydrocarbons of the $C_4$ cut. The use of a methanol excess, to displace the reaction balance, increases the isobutene conversion rate, although the latter conversion is never complete.

The problem of fractionating this mixture by distillation is not simple, since azeotropes form, whose composition is unfavorable: a methanol/MtBE azeotrope and $C_4$ hydrocarbons/methanol azeotropes. The known attempts to fractionate this mixture rely on relatively complex and expensive operations, combining distillations, washings, recyclings, etc.

OBJECTS OF THE INVENTION

A first object of the invention is to increase the conversion rate of isobutene in the $C_4$ cut.

Another object is to improve the purity of MtBE.

A third object is to provide for an inexpensive production and isolation of MtBE.

Other objects will be made apparent from the following description.

SUMMARY OF THE INVENTION

The process of the invention comprises the following essential steps:

(a)—feeding a reaction zone containing an acid etherification catalyst with a $C_4$ cut comprising from 5 to 70% by weight of isobutene, methanol and a recycle stream as hereinafter defined, in the liquid phase, and recovering a reaction effluent, (b)—distilling the reaction effluent under superatmospheric pressure to form a top effluent, containing $C_4$ hydrocarbons, including unconverted isobutene, and methanol, and a bottom effluent containing MtBE, (c)—dividing the top effluent into a first and a second fractions, discharging the first fraction, and recycling the second fraction as the recycle stream to the step (a), and (d)—recovering the bottom effluent of high MtBE content.

DETAILED DISCUSSION

It is clear that the present process operates in contradiction with the principles admitted by the specialists. As a matter of fact, it is conventional in a simple reaction to recycle the unconverted reactant after it has been recovered in a state of relatively high purity (when manufacturing MtBE, it was conventional to recycle methanol after isolation as a relatively pure stream thereof; conversely, the impoverished $C_4$ cut was discharged from the unit); but this is not the case when a reactant is recovered in the dilute state (for example, isobutene in the $C_4$ cut). The recycling of the impoverished $C_4$ cut is contrary to the conventional teachings since it should normally result in a further dilution of isobutene of the charge, thus in a reduction of the isobutene conversion rate.

It has been surprisingly found that this effect is more than compensated by the yield increase due to the renewed passage of isobutene, even though the latter is in a more diluted state. An increase of the global conversion rate of isobutene is observed, together with an increase of the MtBE yield.

The conditions of the etherification reaction are well known: a temperature of 30° to 120° C., preferably 40° to 90° C., and a pressure sufficient to maintain a liquid phase of the reactants.

The catalyst is preferably an ion exchange resin in the acid form, for example, Amberlyst 15 or one of the catalysts described in the U.S. Pat. No. 3,037,052.

One or more reactors of conventional type may be used, for example with a fixed or dispersed bed of catalyst. When operating in two (or more) successive reactors, it is advantageous to proceed at a higher temperature in the first reactor and a lower temperature in the last reactor. The recycling may be effected to the first or to the second reactor.

The molar ratio of methanol to isobutene is usually from 0.9:1 to 2:1, preferably 1.05:1 to 1.4:1.

The distillation of step (b) may be conducted under superatmospheric pressure, for example, 2–40 atmosphere abs. The greatest advantages of the recycling are obtained at a pressure of 7 to 30 atm. abs., particularly 10 to 25 atm. abs.

The effect of the pressure on the composition of the methanol/$C_4$ hydrocarbons azeotropes is known: the higher the pressure, the greater the methanol content.

The azeotropic distillation of analogous mixtures is known, for example, from the patents DE No. 2,705,538 and GB No. 1,176,620; however no suggestion can be found in these documents to perform a recycling step similar to that of the invention.

In the step (c), the ratio by weight (R) of the recycled fraction (second fraction) to the discharged fraction (first fraction) is advantageously from 0.1:1 to 10:1, preferably from 0.3:1 to 3:1. The purity of the MtBE increases with the volume recycled, but a very high purity is not necessary for the use as motor fuel.

The accompanying drawing illustrates the invention, but does not limit its scope.

Two successive reactors 1 and 2 are used. They are fed with the fresh methanol charge and the $C_4$ cut through the duct 3 and with a recycle stream through the duct 4. The effluent is supplied through the duct 5 to the superatmospheric distillation column 6. Practically all the MtBE is recovered from the bottom thereof through the duct 7 and a mixture of methanol with practically all the $C_4$ hydrocarbons is recovered from the top (this mixture is at least partly formed of an azeotrope). This top product is divided into a first fraction, discharged through the duct 8, and a second fraction (recycle fraction), recycled to the reactor 1 through the duct 4. MtBE may be discharged in admixture with a part of the unreacted methanol. This has no serious inconvenience for its use as fuel.

EXAMPLES 1 to 3

12.5 (metric) tons/h of a $C_4$ cut containing 48% b.w. of isobutene and 3.94 t/h of methanol are passed through 2 serially arranged reactors (1 and 2) containing a total of 4 $m^3$ of strongly acidic ion exchanger of the Amberlyst 15 type (a sulfonated polystyrene resin cross-linked with divinylbenzene); this corresponds to a methanol to isobutene molar ratio of 1.15. A variable amount of the $C_4$-methanol azeotrope discharged from the top of a distillation column (6) operated at 15 bars abs. is also recycled to the reactor 1, said azeotrope comprising 7.5% b.w. of methanol and 92.5% b.w. of $C_4$ hydrocarbons. The catalyst is maintained dispersed in the first reactor and in a fixed bed in the second reactor. The average temperature is 90° C. in the first reactor and 60° C. in the second reactor.

It can be deduced from the results given in Table I that an increase of the recycle rate (R), defined as the ratio by weight of this recycled amount (4) to the amount of the discharged distillate (8), greatly increases the performances of the reaction system. The isobutene conversion rate and the production of MtBE increase, while the methanol content of MtBE and the isobutene content of the $C_4$ residual cut decrease. This is the more unobvious as an increase of the methanol content at the inlet of the distillation column (duct 5) is observed.

TABLE I

| EXAMPLE | 1 | 2 | 3 |
|---|---|---|---|
| RECYCLE RATE | 0 | 0.5 | 1 |
| Isobutene conversion | 95% | 96.2% | 97.1% |
| % $CH_3OH$ b.w. in the effluent from the reactors (duct 5) | 4.17 | 4.57 | 4.93 |
| Composition of the distillate (ducts 4 and 8) | | | |
| % $CH_3OH$ b.w. | 7.5 | 7.5 | 7.5 |
| % residual $C_4$ cut b.w. | 92.5 | 92.5 | 92.5 |
| Isobutene content of the residual $C_4$ cut, % b.w. | 4.4 | 3.4 | 2.6 |
| Composition of the MtBE (duct 7) | | | |
| Tons/hour | 8.96 | 9.07 | 9.15 |
| % $CH_3OH$ b.w. | 1.47 | 1.08 | 0.78 |

EXAMPLES 4 to 6

12.5 metric ton/h of a $C_4$ cut containing 50% b.w. of isobutene and 4.46 metric ton/h of methanol are passed through the two serially arranged reactors of example 1; the molar ratio of methanol to isobutene is thus 1.25. Example 4 is effected without recycling; in examples 5 and 6, a part of the $C_4$-methanol azeotrope discharged from the top of the distillation column is recycled to the inlet of the second reactor, the pressure of the column being different in each case. Table II gives the % by weight of methanol in the azeotrope for each pressure of the column.

It is found that the recycling of the distillate to the inlet of the second reactor gives results which are equivalent to or even better than those obtained when recycling it to the inlet of the first reactor.

TABLE II

| EXAMPLE | 4 | 5 | 6 |
|---|---|---|---|
| RECYCLE RATE R | 0 | 1 | 1 |
| DISTILLATION PRESSURE BARS abs. | 15 | 15 | 21 |
| Isobutene conversion % | 95 | 97.5 | 98.3 |
| % b.w. of $CH_3OH$ (duct 5) | 6.3 | 6.3 | 6.7 |
| Composition of the distillate | | | |
| % $CH_3OH$ by weight | 7.5 | 7.5 | 9.2 |
| % residual $C_4$ cut b.w. | 92.5 | 92.5 | 90.8 |
| Isobutene content of the residual $C_4$ cut b.w. | 4.76 | 2.44 | 1.67 |
| Composition of the MtBE | | | |
| Tons/hour | 9.3 | 9.58 | 9.65 |
| % $CH_3OH$ b.w. | 5.4 | 4.6 | 3.1 |

What is claimed:

1. A process for producing methyl tert.-butyl ether, comprising the steps of:
   (a) feeding a $C_4$ cut containing from 5 to 70% by weight of isobutene, methanol, and a recycle stream as hereinafter defined, in liquid phase, to a reaction zone containing an acid etherification catalyst, and recovering a reaction effluent containing methyl tert.-butyl ether, methanol, and unconverted $C_4$ hydrocarbons, including unconverted isobutene;
   (b) distilling the reaction effluent from step (a) under a superatmospheric pressure of from 7 to 30 atmospheres absolute, and separately recovering a top effluent containing $C_4$ hydrocarbons, including unconverted isobutene, and methanol, and a bottom product effluent of high methyl tert.-butyl ether content; and
   (c) dividing the top effluent from step (b) into a first fraction and a second fraction, discharging the first fraction, and recycling the second fraction to step (a) as said recycle stream; wherein the ratio by weight of the second recycled fraction to the first discharged fraction is from 0.1:1 to 10:1.

2. A process according to claim 1, wherein in step (c), said ratio is from 0.3:1 to 3:1.

3. A process according to claim 1, wherein step (a) is effected in at least two successive reactors, the first of which is at a higher temperature than the last one.

4. A process according to claim 1, wherein step (a) is effected in at least two successive reactors, at least the first reactor having a catalyst dispersed in the liquid phase and at least the last reactor having a fixed bed of catalyst.

5. A process according to claim 1, wherein said distillation pressure is from 10 to 25 atmospheres absolute.

6. A process according to claim 1, wherein step (a) is effected in at least two successive reactors and the recycle stream is fed directly to the second reactor.

7. A process according to claim 1, wherein in step (a), the ratio of methanol to isobutene is from 0.9:1 to 2:1.

8. A process according to claim 7, wherein said ratio of methanol to isobutene is from 1.05:1 to 1.4:1.

9. A process according to claim 2, wherein in step (b), the isobutene content of said top effluent is not higher than 3.4% by weight.

* * * * *